United States Patent
Sahin et al.

(10) Patent No.: US 12,208,117 B2
(45) Date of Patent: Jan. 28, 2025

(54) GLYCEROL AND SODIUM PENTABORATE BASED FORMULATION PREVENTING POSTOPERATIVE ADHESIONS

(71) Applicant: YEDITEPE UNIVERSITESI, Istanbul (TR)

(72) Inventors: Fikrettin Sahin, Istanbul (TR); Mustafa Erhan Aysan, Istanbul (TR); Okan Demir, Istanbul (TR)

(73) Assignee: YEDITEPE UNIVERSITESI

(*) Notice: Subject to any disclaimer, the term of this patent is extended or adjusted under 35 U.S.C. 154(b) by 574 days.

(21) Appl. No.: 17/614,386

(22) PCT Filed: May 29, 2020

(86) PCT No.: PCT/TR2020/050466
§ 371 (c)(1),
(2) Date: Nov. 26, 2021

(87) PCT Pub. No.: WO2020/242424
PCT Pub. Date: Dec. 13, 2020

(65) Prior Publication Data
US 2022/0226370 A1    Jul. 21, 2022

(30) Foreign Application Priority Data
May 30, 2019 (TR) .................. 2019/08285

(51) Int. Cl.
*A61K 33/22* (2006.01)
*A61L 31/14* (2006.01)
*A61L 31/16* (2006.01)

(52) U.S. Cl.
CPC .............. *A61K 33/22* (2013.01); *A61L 31/14* (2013.01); *A61L 31/16* (2013.01); *A61L 2300/102* (2013.01); *A61L 2300/22* (2013.01)

(58) Field of Classification Search
None
See application file for complete search history.

(56) References Cited

U.S. PATENT DOCUMENTS 3,988,157 A * 10/1976 Van Paesschen ........ C08J 7/056
427/407.1
5,364,756 A * 11/1994 Livesey ............... A01N 1/0221
435/235.1

(Continued)

FOREIGN PATENT DOCUMENTS

CN        102949754 A      3/2013
JP      2001278788 A  *  10/2001
(Continued)

OTHER PUBLICATIONS

Blasdale et al. Journal of the American Chemical Society 1939 61(4): 917-920 (Year: 1939).*

(Continued)

*Primary Examiner* — Melissa S Mercier
*Assistant Examiner* — Caralynne E Helm
(74) *Attorney, Agent, or Firm* — Bayramoglu Law Offices LLC

(57) ABSTRACT

A glycerol and sodium pentaborate based formulation developed for preventing postoperative adhesions occurring between manipulated tissues and organs is provided. An objective of the glycerol and sodium pentaborate based formulation is to provide a formulation comprising a mixture of glycerol, wherein the glycerol is one of the most abundant biomolecules in a human body, and sodium pentaborate, wherein the sodium pentaborate is known to have positive effects on a wound healing, with a purpose of preventing the postoperative adhesions.

4 Claims, 2 Drawing Sheets

(56) References Cited

U.S. PATENT DOCUMENTS

| | | | | |
|---|---|---|---|---|
| 9,962,405 B2 * | 5/2018 | Sahin | ............... | A61K 9/06 |
| 2011/0008619 A1 * | 1/2011 | Murphy | ............... | D21H 21/14 |
| | | | | 428/688 |
| 2013/0267479 A1 * | 10/2013 | Jamois | ............... | C07F 5/04 |
| | | | | 514/64 |

FOREIGN PATENT DOCUMENTS

| | | | |
|---|---|---|---|
| RU | 2016122764 A | 12/2017 | |
| WO | 2014168595 A1 | 10/2014 | |
| WO | WO-2018063118 A2 * | 4/2018 | ............ B65D 81/28 |

OTHER PUBLICATIONS

Erhan Aysan, et al., Efficacy of glycerol in preventing postoperative peritoneal adhesions, Japan Society of Obstetrics and Gynecology Research, 2010, pp. 639-645, vol. 36, No. 3.

* cited by examiner

GLYCEROL AND SODIUM PENTABORATE BASED FORMULATION PREVENTING POSTOPERATIVE ADHESIONS

CROSS REFERENCE TO THE RELATED APPLICATIONS

This application is the national stage entry of International Application No. PCT/TR2020/050466, filed on May 29, 2020, which is based upon and claims priority to Turkish Patent Application No. 2019/08285, filed on May 30, 2019, the entire contents of which are incorporated herein by reference.

TECHNICAL FIELD

The present invention relates to a glycerol and sodium pentaborate based formulation developed for preventing postoperative adhesions occurring between the manipulated tissues and organs.

BACKGROUND

After any kind of surgical intervention performed on living organisms, when the tissues that are cut in the operated site are healing, adhesions occur between the organs and tissues that are located at that site or neighboring that site due to fibrosis in the early period and collagen tissue accumulation in the late period. The resulting collagen tissue and the amount of adhesions depending thereon vary depending on many parameters such as the size and duration of the surgical intervention, whether the environment is infected, whether a foreign body (prosthetic material) is used, the amount of bleeding and the immune response power of the patient. However adhesions definitely occur after every surgical intervention.

Post-operative adhesions are a serious problem after any type of surgical intervention. The most common cause of intestinal obstruction, the most common cause of secondary laparotomy after abdominal operations, and the most common cause of female infertility are postoperative adhesions. Many studies are carried out to solve this serious problem. In the studies in the literature, liquid or soluble gelatinous materials with different contents and active substances that are absorbed over time are placed at the surgical site, but there is no definitive solution to the problem.

In applications performed in the prior art, liquid or soluble solid materials cause adhesions by inducing a natural foreign body reaction in the organism as they are not fully absorbed from the medium. These either directly damage the tissues they contact or the active substances they contain are insufficient to prevent adhesion formation.

SUMMARY

The objective of the present invention is to prevent postoperative adhesions, and in this context, to form a formulation comprising a mixture of glycerol, which is one of the most abundant biomolecules in the human body, and sodium pentaborate, which is known to have positive effects on wound healing.

This formulation is intended to act through blocking excessive fibrosis and collagen production occurring in the surgical site and accelerating wound healing.

BRIEF DESCRIPTION OF THE DRAWINGS

"A Glycerol and Sodium Pentaborate Based Formulation Preventing Postoperative Adhesions" developed to fulfill the objectives of the present invention is illustrated in the accompanying figures, in which.

DETAILED DESCRIPTION OF THE EMBODIMENTS

The glycerol and sodium pentaborate based formulation of the present invention is used for preventing adhesions between the tissues and organs that are manipulated at the surgical site as a result of any kind of surgical intervention. This formulation described within the scope of the present invention is a mixture of glycerol, which is one of the most abundant biomolecules in the human body, and sodium pentaborate, which is known to have positive effects on wound healing. These two substances prevent postoperative adhesions thanks to both biocompatibility thereof and their positive effects on wound healing through blocking excessive fibrosis and collagen production.

Glycerol that is discussed within the scope of the invention is the main substance of the ester named triglyceride, which is the most abundant biomolecule in humans, animals and plants. Sodium pentaborate, which is another component, is a boron-based compound. Boron is a nonmetallic element with atomic number five and atomic weight of 10.8; and as it is located next to the carbon atom, which is the primary element of life, in the periodic table, it is very similar to this atom with its physical and chemical properties. Since boron is a very stable atom, it is not found free in nature and is generally found in a form called borate formed by its binding with $O_2$. Borates are odorless white crystals and dissolve immediately in water. The simplest borates are boron oxide ($B_2O_3$) and boric acid ($H_3BO_3$).

The formulation of the present invention is a suspension of glycerol with a concentration of 1% to 10% and sodium pentaborate with a concentration of 1% to 10% in physiological saline solution or another inert and biocompatible liquid. The formulation particularly preferred within the scope of the invention is comprised of 1% glycerol and 3% sodium pentaborate. The suspension containing the formulation of the present invention is sprayed after any surgical intervention on the surfaces, where the surgery is performed, and where the hand of the surgeon or the surgical instruments used during the operation contact, and full contact thereof with these surfaces is ensured by applying light friction via hand for at least one minute. Then, using routine techniques, the wound is closed as the surgeon deems appropriate. The formulation prevents formation of postoperative adhesions by forming a layer on the surfaces of the tissues that it contacts for about 48-72 hours, and thereby, on one hand, preventing contact of these surfaces with the surrounding tissues, and on the other hand, accelerating wound healing on these surfaces and blocking excessive fibrosis and collagen tissue production.

Figure 1:
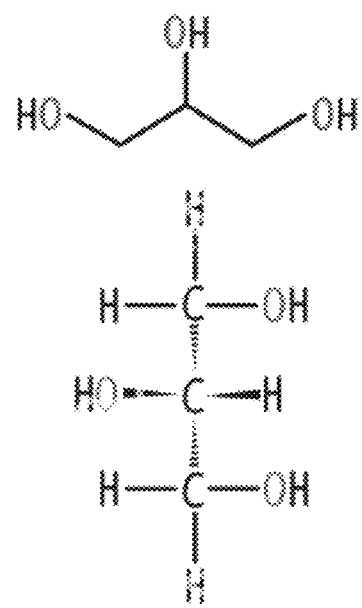
FIG. 1 is a representation of the Glycerol formula.
Figure 2:
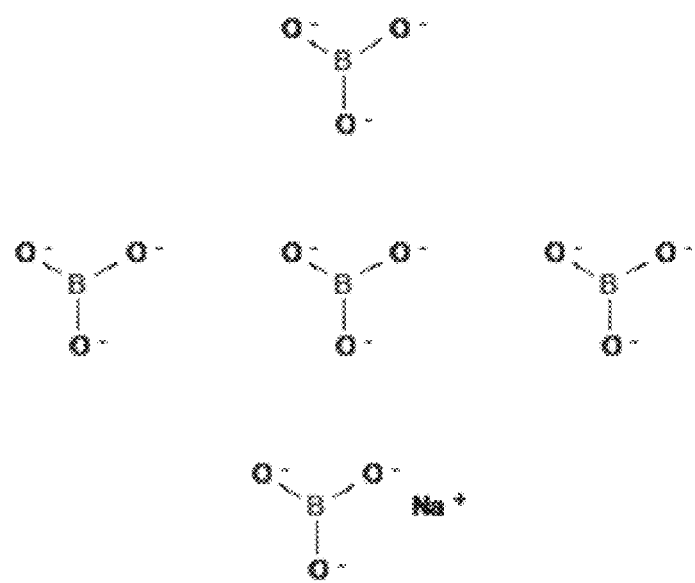
FIG. 2 is a representation of the Sodium Pentaborate formula.
Figure 3:
FIG. 3 is a representation of a case wherein the liquid of the present invention is not applied on the operated rat and there is an intense adhesion.

In the experimental study conducted on rats, after the adhesion model application on the rat cecum tissue, the omentum tissue adhered to the cecum as seen in FIG. 3.

Figure 4:
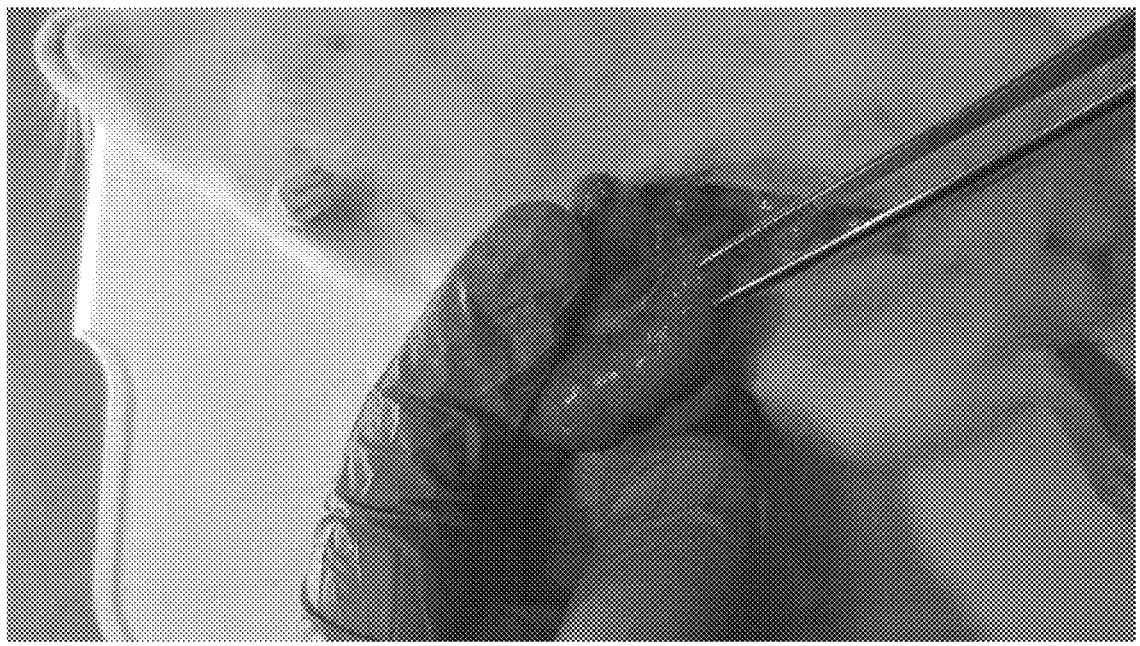
FIG. 4 is a representation of a case wherein the liquid of the present invention is applied on the operated rat and no adhesion is observed.

However, it was observed that there was no adhesion to the cecum tissue in rats to which the formulation of the invention was applied (FIG. 4).

What is claimed is:

1. A glycerol and sodium pentaborate based formulation consisting of a mixture of glycerol and sodium pentaborate in a physiological saline solution, wherein the glycerol and sodium pentaborate based formulation blocks fibrosis and collagen production, preventing adhesion between tissues and organs manipulated at a surgical site as a result of surgical intervention.

2. The glycerol and sodium pentaborate based formulation according to claim 1, wherein the glycerol has a concentration varying between 1% and 10%.

3. The glycerol and sodium pentaborate based formulation according to claim 1, wherein the sodium pentaborate has a concentration varying between 1% and 10%.

4. The glycerol and sodium pentaborate based formulation according to claim 1, wherein the glycerol and sodium pentaborate based formulation is in the form of a spray.

* * * * *